(12) United States Patent
Masini

(10) Patent No.: US 6,206,884 B1
(45) Date of Patent: Mar. 27, 2001

(54) REDUCTION-BASED JOINT REPLACEMENT APPARATUS AND METHODS

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 0 days.

(21) Appl. No.: 09/115,960

(22) Filed: Jul. 15, 1998

(51) Int. Cl.$^7$ .............................. A61B 17/90; A61F 2/46
(52) U.S. Cl. .......................................... 606/89; 623/22.12
(58) Field of Search ................. 606/87, 89, FOR 96, 606/FOR 102, 96 US, 102 US; 623/19.11, 20.11, 20.14, 20.15, 22.11, 22.42, 23.47, 22.12

(56) References Cited

U.S. PATENT DOCUMENTS

| | | | |
|---|---|---|---|
| 3,814,089 | * | 6/1974 | Deyerle ............................. 606/89 X |
| 5,690,637 | * | 11/1997 | Wen et al. ............................. 606/88 |
| 5,885,297 | * | 3/1999 | Matsen ................................. 606/87 |

FOREIGN PATENT DOCUMENTS 2 737 848 A1 * 2/1997 (FR) ..................................... 623/20

* cited by examiner

Primary Examiner—David H. Willse
(74) Attorney, Agent, or Firm—Gifford, Krass, Groh, Sprinkle, Anderson & Citkowski, PC

(57) ABSTRACT

A reduction-based orthopedic system facilitates the installation of a properly oriented prosthetic component of the type having an articulating surface adapted to co-act in a joint. A trialing component attachable to an anchoring unit includes an articulating surface corresponding to that of the prosthetic component, enabling a desired orientation to be established through a trial reduction. A cutting guide is provided which is physically indexed to the trialing component and the prosthesis, such that when the bone is modified using the guide, the prosthetic component automatically assumes the desired orientation. The apparatus invention may further include apparatus for locking the trialing component into place upon establishing the desired orientation, with the anchoring unit being rigidly coupleable to the anchoring unit bone through attachment to the trialing component in locked position. In an alternative configuration, the bone-cutting guide is coupleable to the anchoring unit through direct attachment.

5 Claims, 5 Drawing Sheets

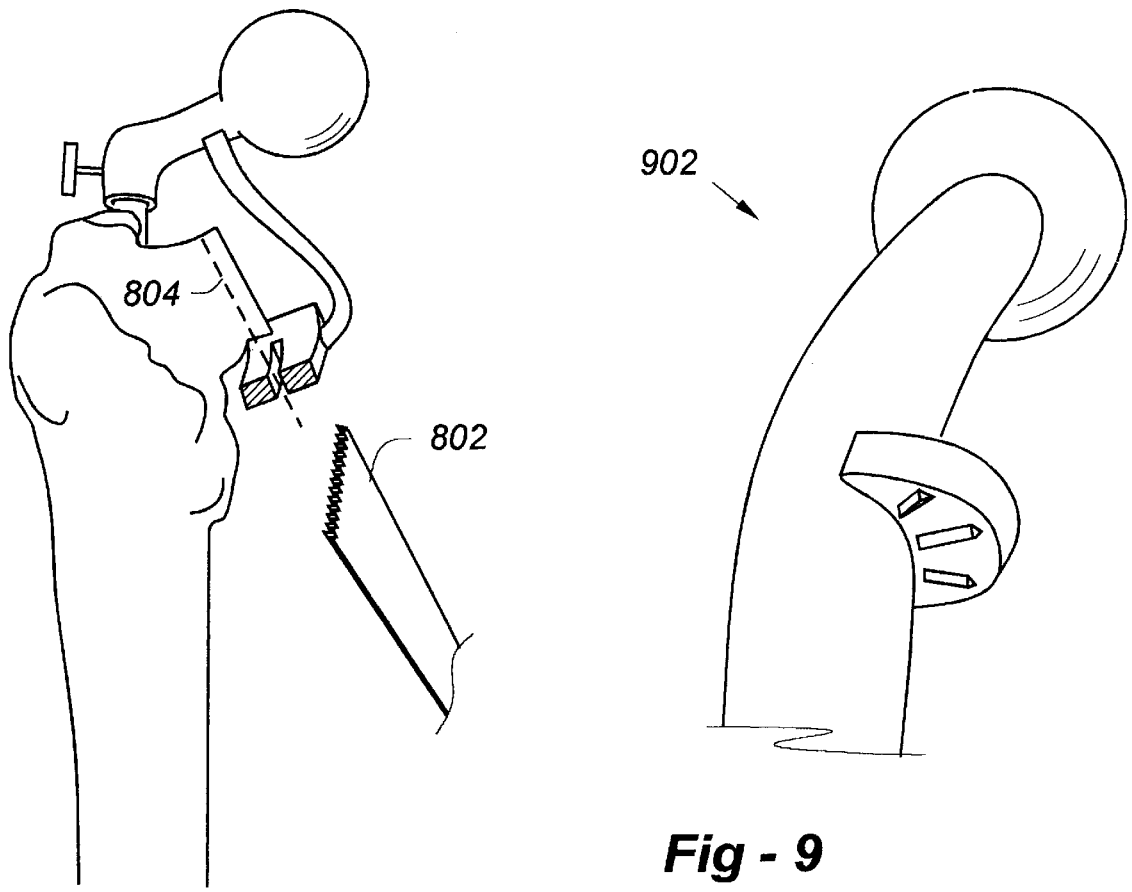
Fig - 8
Fig - 9
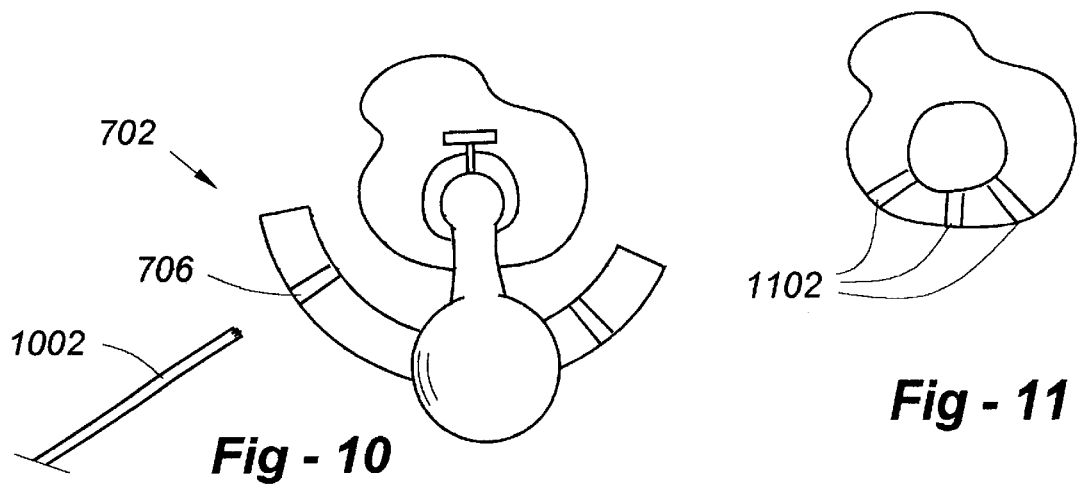
Fig - 10
Fig - 11

REDUCTION-BASED JOINT REPLACEMENT APPARATUS AND METHODS

FIELD OF THE INVENTION

This invention relates generally to the field of arthroplasty and, in particular, to methods and apparatus associated with joint replacement, including total hip replacement, using joint reduction as a means to determine optimum positioning of the prosthesis.

BACKGROUND OF THE INVENTION

In total hip replacement, that is, wherein both the ball and socket portions of the hip are replaced with prosthetic components, it is now conventional to use an implant having an intramedullary stem on the femoral side. This stem transitions into a neck and terminates into the ball portion, which engages with acetabulum of the pelvis.

For many reasons, it is difficult to align the components associated with total hip replacement prior to fixation. As a result, the surgical protocol used in conjunction with such procedures often resorts to considerable trial-and-error positioning steps, freehand trimming of host bone, and other time-consuming imprecise steps based largely on the skill and experience of the attending physician. Although modular implants are now used which permit incremental changes in leg length through tapered head attachment to the neck of the stem, many complications have arisen out of such modularity, including dissociation, wear, osteolysis, and implant fracture. Without question any process or instrumentation capable of bringing about more predictable results and accurate alignment in a shorter period of time would be welcome by the medical community.

SUMMARY OF THE INVENTION

This invention resides in methods and apparatus associated with the installation of a properly oriented prosthetic component of the type having an articulating surface adapted to co-act in a joint. The preferred apparatus includes an anchoring unit rigidly connectable to the bone, and a trialing component attachable to the anchoring unit. The trialing component includes an articulating surface corresponding to that of the final implant, enabling a desired orientation of the implant to be established through trial reduction. A cutting guide is provided which is physically indexed to the trialing component, such that when the bone is modified using the guide, a desired implant orientation and joint function may be automatically achieved when the prosthetic component is ultimately installed.

The invention is applicable to a variety of joint situations, particularly ball-and-socket type joint characteristic of the hip and shoulder. In such situations, the anchoring unit is preferably coupled to the bone through implantation within an intramedullary canal. Indeed, the anchoring unit may take the form of a tool of the type typically used to prepare the canal, such as a reamer, broach, or trial stem.

In one configuration, the inventive apparatus further includes means for locking the trialing component into place upon establishing a desired implant orientation and/or joint function, with the anchoring unit being rigidly coupled to the anchoring unit bone through attachment to the trialing component in a locked position. In a different configuration, the bone-cutting guide is coupleable to the anchoring unit through direct attachment to the connection point.

Based upon such apparatus, a method of modifying a bone to receive a prosthetic component according to the invention preferably includes the steps of:

connecting an adjustable trialing component to the bone;
reducing the bone with the trialing component attached to test the joint;
adjusting the position of the trialing component during the trial reduction to achieve a desired orientation;
installing a cutting guide which is physically indexed to the desired orientation established with the trialing component;
modifying the bone using the cutting guide to provide a seating surface; and
installing the prosthetic component such that when at least a portion of the component engages with the seating surface, the prosthetic component assumes the desired orientation

BRIEF DESCRIPTION OF THE DRAWINGS

FIG. 8 illustrates how, with the cutting guide of FIG. 7 properly installed onto the head/neck component, a saw may be used to adjust neck length;

FIG. 9 illustrates a preferred collared femoral component adapted for use with the invention having anti-rotation positioning means;

FIG. 10 is a top view of a femoral trial and attached cutting guide, showing how the rim of a resected neck may be notched to receive the anti-rotation means of the femoral component of FIG. 9;

FIG. 11 is a top view of a femur illustrating a set of completed anti-rotation notches;

DETAILED DESCRIPTION OF THE INVENTION

This invention is directed toward joint trialing and bone-cutting apparatus utilizing joint reduction as a means for determining the final positioning of a prosthetic component such as a collared femoral hip unit. As used herein, the term "joint reduction" means that the mating portion of the joint being constructed permits the trialing procedure prescribed by the invention, thereby establishing a correct joint implant orientation through in-joint testing.

Broadly, an anchoring device is temporarily implanted or otherwise connected to the bone destined to receive the prosthesis. The anchoring device is configured to removeably receive a trialing unit and one or more bone-modification instruments physically indexed to the trialing unit and the final implant. By having these various components physically coordinated with one another, a bone may be modified in accordance with a desired orientation established through a trial joint reduction so the final implant readily assumes the orientation upon fixation.

In a preferred embodiment, the anchoring device takes the form of an intramedullary shaping tool, a broach, reamer or trial stem, and the trialing unit takes the form of femoral head or head/neck component for use in total hip arthroplasty. It will be apparent to the skilled practitioner, however, that the invention is applicable to other joint situations, particularly those involving ball-and-socket type interfaces as found in the shoulder and elsewhere in the body.

Figure 1:
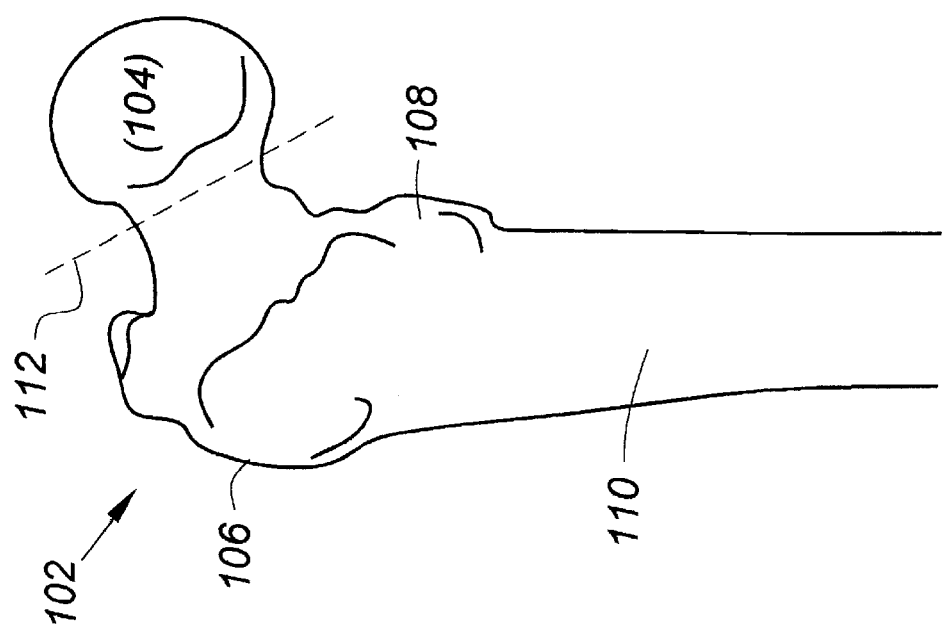
FIG. 1 is a side-view illustration of a proximal femur indicating a provisional cut carried out in conjunction with a method of the invention.

Turning now to the drawings, FIG. 1 begins a sequence of illustrations which depict a preferred method of the invention, using novel instrumentation and other apparatus. FIG. 1 shows the proximal end of a femur generally at 102, having a ball end 104 transitioning into a shaft 110. Also visible are the greater and lesser trochanters, 106 and 108, respectively. In this case, the head portion 104 is to be removed and replaced with a prosthesis having an intramedullary stem, as depicted in subsequent drawings.

As an initial step, the ball portion 104 is resected at a point along the neck as shown with broken line 112. This initial resection is preferably selected so as to be just below the ball portion, or, at least, leaving the neck long enough to allow for subsequent, more accurate trimming to receive the final implant in a precise orientation determined through the trial reduction.

Figure 2:
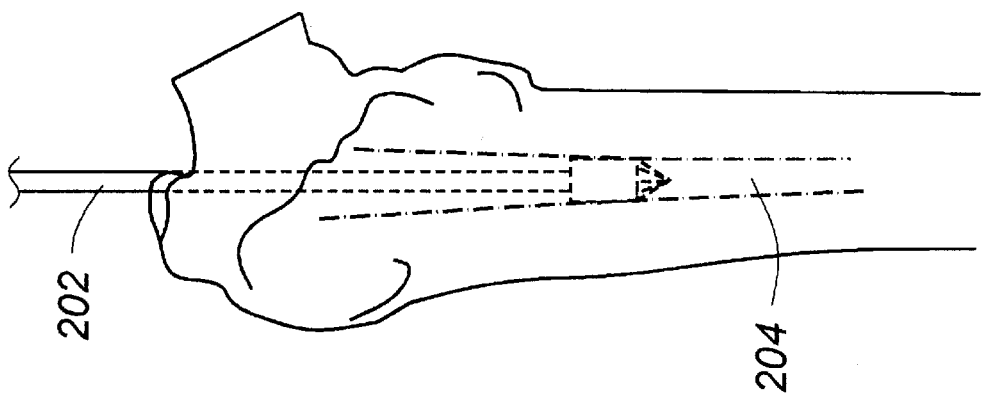
FIG. 2 illustrates reaming, if desired, of the intramedullary canal.
Figure 3:
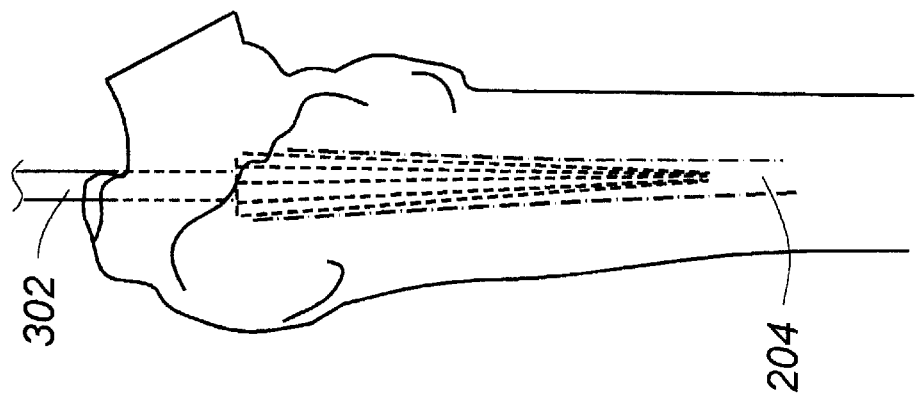
FIG. 3 illustrates the use of a broach, as appropriate, to prepare the bone to receive an appropriately sized stem.
Figure 4:
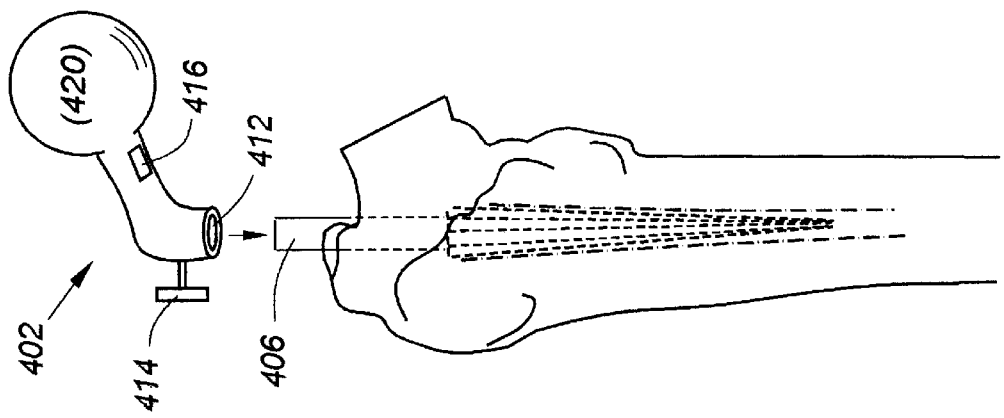
FIG. 4 illustrates a preferred embodiment of the invention wherein a trial head/neck assembly is installed onto an exposed broach left in place.

Having removed the ball portion from the proximal femur, the intramedullary canal 204 is prepared, as necessary, for example, using a reamer 202, as shown in FIG. 2 and/or broach 302, as shown in FIG. 3. Typically, a set of broaches, each with an increasingly larger diameter, is used according to such procedures and, assuming this is the case, the last or final broach 406 is left in place, as shown in FIG. 4.

The tool used in manipulating the broach, whether manual or electrically powered, is then removed, leaving an upwardly oriented exposed stem, onto which an adjustable head assembly 402 according to the invention is installed. Notably, this assembly 402 includes an aperture 412 to receive the exposed stem of the last broach (or other anchoring unit remaining in the intramedullary canal), a manually operable locking mechanism such as handle 414, and one or more attachment points associated with the aligned interconnection of a cutting jig or other devices described below.

Figure 6:
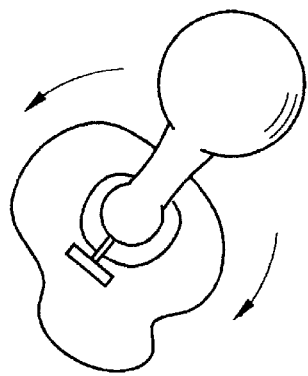
FIG. 6 is a drawing which illustrates how the test joint reduction may proceed in terms of rotational or anteversion adjustment.
Figure 5:
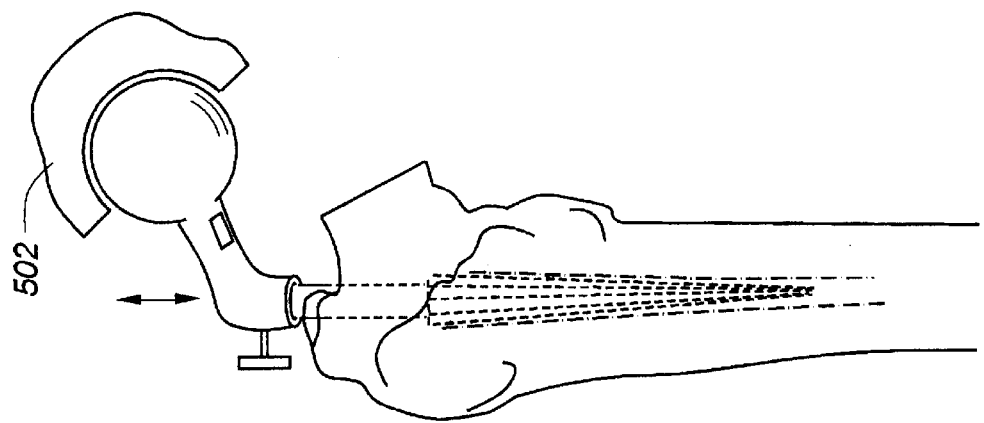
FIG. 5 is a drawing which shows how the head/neck component of FIG. 4 may be incorporated into a trial reduction to test the joint.

In the embodiment currently being described, the attachment point takes the form of a non-circular aperture 416, with the understanding that other connection mechanisms enabling a geometrically stabilized interconnection may alternatively be used. In addition to the features just described, the head assembly 402 includes a ball portion 420 used for trialing purposes, as best understood with respect to FIGS. 5 and 6. In particular, FIG. 5 illustrates how the trialing component 402 may be moved up and down onto the installed anchoring unit to adjust for length, whereas FIG. 6 illustrates how the trialing component may be rotated to adjust for anteversion, in the case of a hip replacement. Although the procedures illustrated in FIGS. 5 and 6 may be carried out apart from a trial reduction, importantly, according to the invention such adjustments may be made during a trial reduction, that is, with the articulating surface of the trialing component being engaged with the corresponding surface of the joint, namely the acetabulum 502, again, in the case of a hip replacement.

Figure 7:
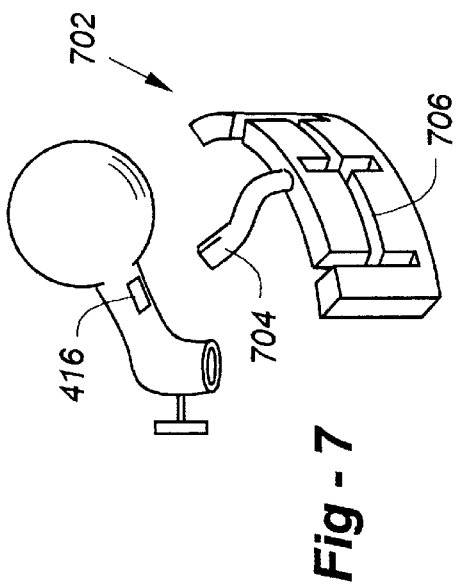
FIG. 7 is an illustration which shows how a cutting guide is attached to the trial head/neck component to realize a particular neck length resection.

Once a desired orientation is achieved which is representative of a desired or optimum joint function, the trialing component may be locked into position through the use of manually operable means such as handle 414. Once locked into this desired orientation, as shown in FIG. 7, a cutting guide 702 may be fitted into the aperture 416 by way of a mating insert 704, thereby physically indexing the cutting guide 702 not only to the trialing component but, while locked through the anchoring unit, the cutting guide is rigidly coupled and indexed to the bone itself. It should be apparent at this point that the hip may be dislocated to facilitate placement of the cutting guide and actual resection at this stage; that is, the joint may dislocated or reduced to make the appropriate modification to the bone.

As such, as seen in FIG. 8, with a bone-modification instrument such as saw blade 802 engaging with the guide, a new resection 804 may be carried out to receive a properly designed final prosthetic component in a manner so as to automatically assume the desired orientation and joint function established through the trial reduction. In this way, as opposed to the use of modular components to adjust neck length, the "modularity" is built into the inventive instrumentation, facilitating an infinite number of positions within a desired range of joint function.

Although existing conventional implants, particularly "collared" implants for use in femoral hip replacement, may be employed in conjunction with the invention, a prosthetic component having a collar 904 specifically tailored for both height and rotation is preferably utilized. The proximal end of just such a bone is illustrated generally at 902 in FIG. 9, wherein the collar 904 includes one or more downwardly oriented protrusions 906, the function of which is perhaps best understood with reference to FIGS. 10–12, FIG. 12 in particular.

Figure 12:
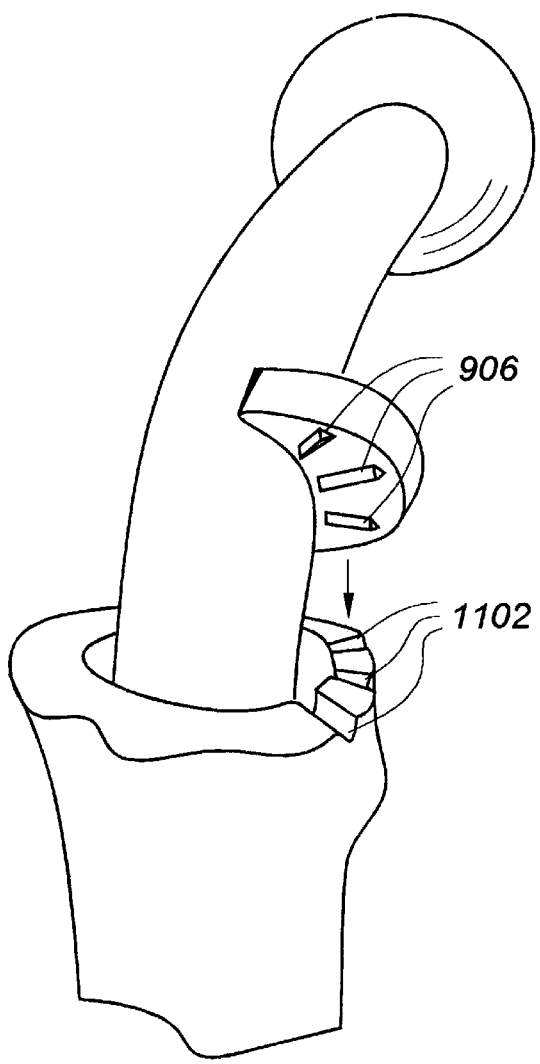
FIG. 12 is a drawing which shows how the femoral component of FIG. 9 cooperates with the notched bone of FIG. 11.

Making reference to FIG. 10, which is a top-down view of a proximal femur having the trialing component and cutting guide in a locked position, the saw blade 1002 may now be introduced at an angle more or less transverse to that used to perform the resection 804. Use of the saw in this manner results in the formation of corresponding notches 1102 shown in FIG. 11. Having formed the resection 804 and the notches 1102 in accordance with the stabilized cutting guide, the prosthetic component 902 may now be installed as shown in FIG. 12.

Though perhaps not measurable from the figures, knowing the various dimensions of the cutting guide relative to the articulating surface of the trialing component in advance, by using the cutting guide rigidly coupled to the trialing component as taught herein, the formation of the resected surface 804 and the notches 1102 are in precise alignment relative to the bottom surface of the collar 904 and projections 906, such that when a mating correspondence is established and the prosthetic component is fixed into place, the articulating surface of the ball portion of the prosthetic component assumes the same orientation as articulating surface of the trialing component, thereby automatically achieving a desired joint orientation.

Figure 13:
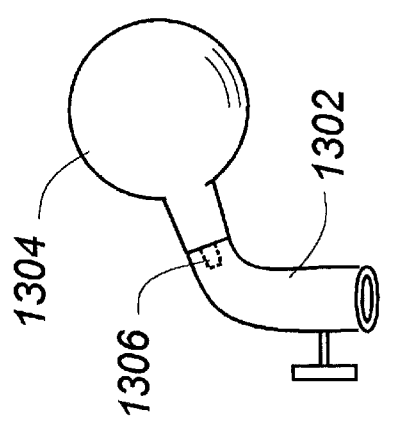
FIG. 13 illustrates an alternative embodiment of the invention having a separately removable head component.

As opposed to, or in addition to, making attachment to a single connection point anchoring unit, which may take the form of an intramedullary canal preparation tool, connection may also be made at different points along whatever mechanism is used between the physical connection to the bone and the articulating surface of the trial component. For example, as shown in FIG. 13, an adjustable collar 1302 may be provided, onto which different devices may be removably attached, such as a trialing component 1304 through an additional point of connection 1306. Preferably, the connection point 1306 assumes a preferential orientation as through the use of a non-round host and aperture or other type of keyway.

Figure 15:
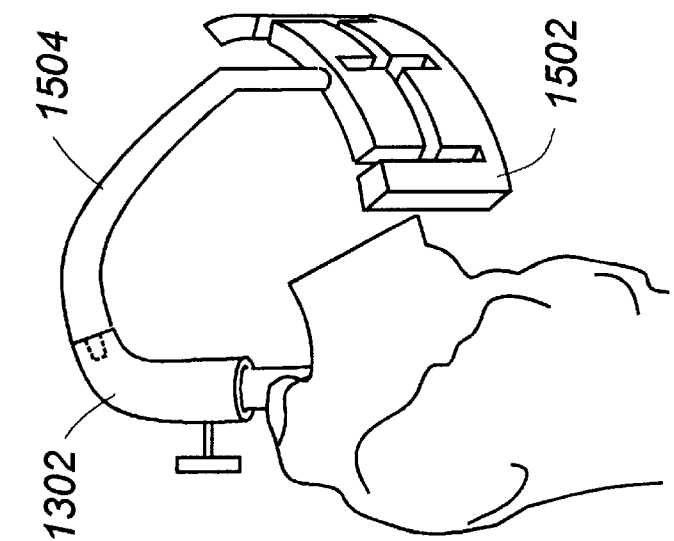
FIG. 15 illustrates the attachment of a cutting guide in place of the head component of FIG. 13.
Figure 14:
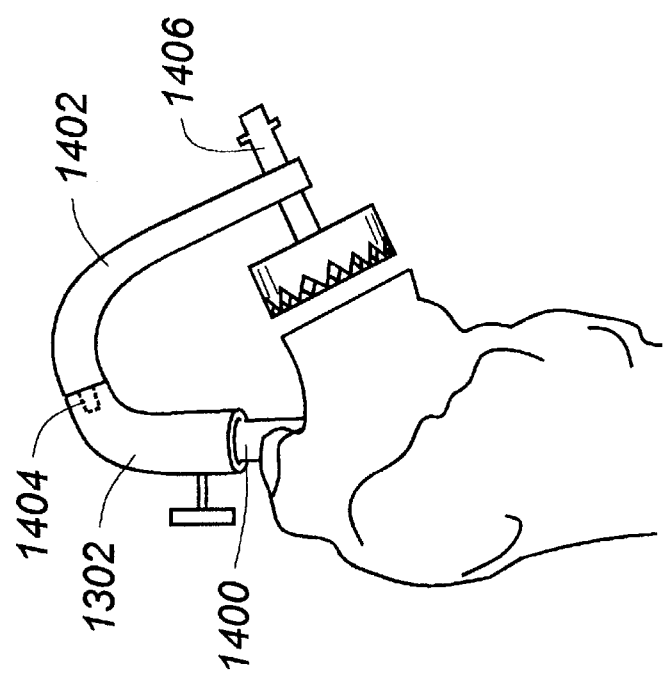
FIG. 14 illustrates how, with the head component of FIG. 13 removed, one of a variety of bone-shaping tools may be installed.

In FIG. 14, the collar 1302 has been adjustably installed onto a connection point 1400 extending from the bone to be modified, and now, with the trialing component removed, assuming a desired orientation has been achieved through trial reduction, different types of jigs may be installed at point 1404, such as the arm 1402 to which a router, calcar reamer or other types of instrumentation may be deployed. The stop 1406 is provided to ensure that a desired depth of modification is achieved. In FIG. 15, the trialing component has been replaced with a bone-cutting guide having an arm 1504 interconnected to the collar or sleeve 1302, terminating a slotted piece 1502 which may be similar, if not identical to that shown in FIG. 7.

Figure 16:
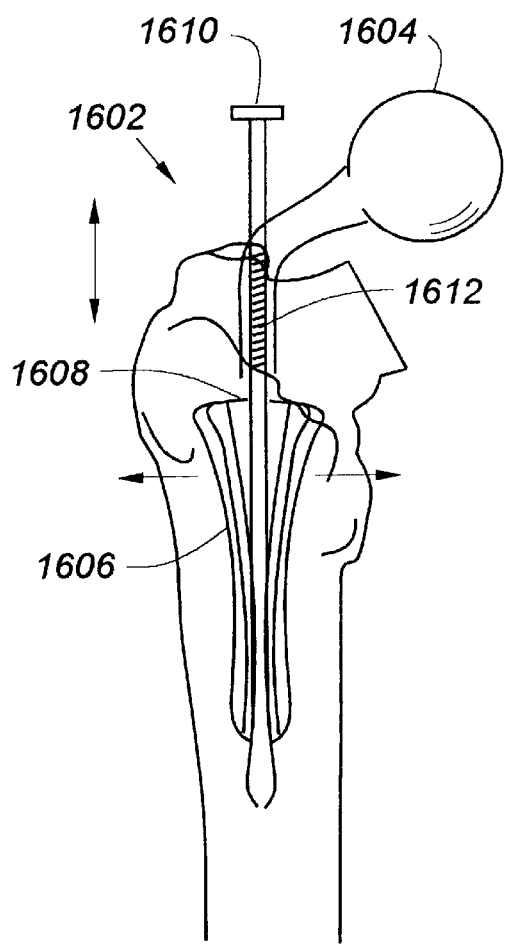
FIG. 16 illustrates yet a further embodiment of the invention incorporating a means to move and fix an entire assembly in conjunction with variously configured cutting guides.

FIG. 16 illustrates yet a further alternative embodiment of the invention wherein an entire stem/neck/head unit shown generally at 1602 is preferably adjustable in multiple dimensions including up-and-down and rotationally, prior to being locked into place with rod 1610 having threads 1612. In this particular embodiment, advancement of the rod 1610 moves downwardly and into the canal of the bone, and the stem 1608 includes expandable side portions such as fins 1606 or other features which protrude outwardly as shown, to hold the device in position as determined through trial reduction.

Having achieved a desired orientation, the trialing head unit 1604 may be removed and into the locked stem there may be placed one or more jigs, fixtures or cutting guides to trim the neck in a manner such that when the prosthetic component is ultimately installed, it will be properly indexed to the articulating surface of the trialing component 1604 in a manner which is physically indexed and coordinated with the desired orientation and joint function.

I claim:

1. Apparatus for modifying a bone to receive a prosthetic component having an articulating surface adapted to co-act in a joint, comprising:

an anchoring unit rigidly connectable to the bone;

a separate, adjustable trialing component removably attachable to the anchoring unit, the trialing component including an articulating surface corresponding to that of the prosthetic component, enabling a desired orientation to be established through trial joint reduction and adjustment of the trialing component; and a bone-cutting guide couplable to one of the anchoring unit and the trialing component, the guide being physically indexed to the trialing component, such that when the bone is modified using the guide, the desired final implant orientation is achieved when the prosthetic component is installed.

2. The apparatus of claim 1, wherein the prosthetic component is a proximal femoral implant.

3. The apparatus of claim 1, wherein the prosthetic component is a proximal humeral implant.

4. The apparatus of claim 1, further including means for locking the trialing component into place upon establishing the desired orientation.

5. The apparatus of claim 1, wherein the bone-cutting guide is coupleable to the anchoring unit.

* * * * *